United States Patent
Rodriguez Dehli et al.

(10) Patent No.: US 8,859,770 B2
(45) Date of Patent: Oct. 14, 2014

(54) PROCESS FOR PREPARING [4,6-BIS-DIMETHYLAMINO-2-[4-(4-TRIFLUORO-METHYLBENZOYLAMINO)BENZYL]-PYRIMIDIN-5-YL]ACETIC ACID

(75) Inventors: Juan M. Rodriguez Dehli, Mainz (DE); Michael Schul, Lahnstein (DE); Christian Stange, Ingelheim (DE); Robert Hagenkoetter, Huenstetten (DE); Xiao-Jun Wang, Ridgefield, CT (US); Li Zhang, New Milford, CT (US); Oriol Massot, Malgrat De Mar (ES)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/116,876

(22) PCT Filed: May 7, 2012

(86) PCT No.: PCT/EP2012/058338
§ 371 (c)(1),
(2), (4) Date: Mar. 5, 2014

(87) PCT Pub. No.: WO2012/156221
PCT Pub. Date: Nov. 22, 2012

(65) Prior Publication Data
US 2014/0187779 A1    Jul. 3, 2014

Related U.S. Application Data

(60) Provisional application No. 61/486,363, filed on May 16, 2011.

(51) Int. Cl.
*C07D 239/48* (2006.01)

(52) U.S. Cl.
CPC .................................... *C07D 239/48* (2013.01)
USPC .......................................................... 544/329

(58) Field of Classification Search
USPC .................................. 544/322, 329
See application file for complete search history.

(56) References Cited

FOREIGN PATENT DOCUMENTS

WO    WO 2004096777 A1 * 11/2004    ........... C07D 239/42

* cited by examiner

*Primary Examiner* — Kristin Vajda
(74) *Attorney, Agent, or Firm* — Michael P. Morris; Timothy X. Witkowski

(57) ABSTRACT

The present invention relates to a process for preparing a compound of formula (I).

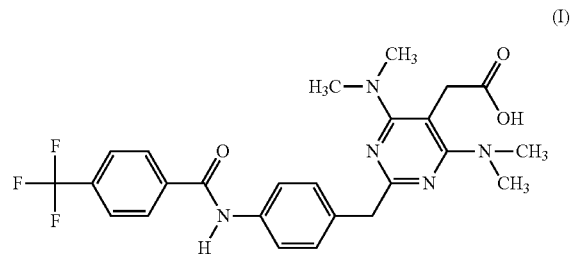

18 Claims, No Drawings

PROCESS FOR PREPARING [4,6-BIS-DIMETHYLAMINO-2-[4-(4-TRIFLUORO-METHYLBENZOYLAMINO)BENZYL]-PYRIMIDIN-5-YL]ACETIC ACID

The present invention relates to a process for preparing a compound of formula (I),

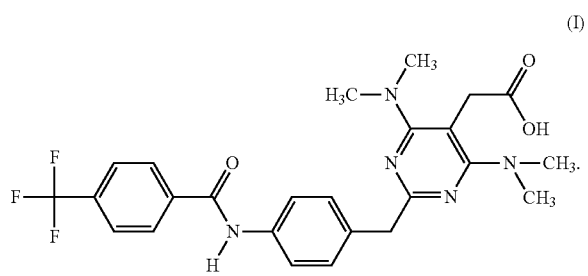 [SMILES: CN(C)c1nc(Cc2ccc(NC(=O)c3ccc(C(F)(F)F)cc3)cc2)nc(N(C)C)c1CC(=O)O]

WO 2004096777 discloses the use of the compound of formula (I) as CRTH2 antagonist as well as a process for preparing said compound in small amounts.

It is an objective of the present invention to provide a process suitable for large scale production of the compound of formula (I). Said process should provide the compound of formula (I) in high yield and high purity. Said process further should be efficient in terms of effort, energy and expenses.

The present invention relates to a process for preparing a compound of formula (I),

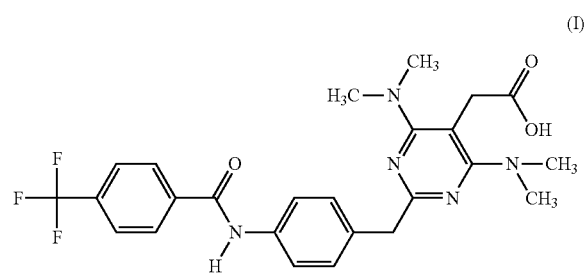 [SMILES: CN(C)c1nc(Cc2ccc(NC(=O)c3ccc(C(F)(F)F)cc3)cc2)nc(N(C)C)c1CC(=O)O]

wherein the compound of formula (I) is obtained from hydrolysis of a compound of formula (II)

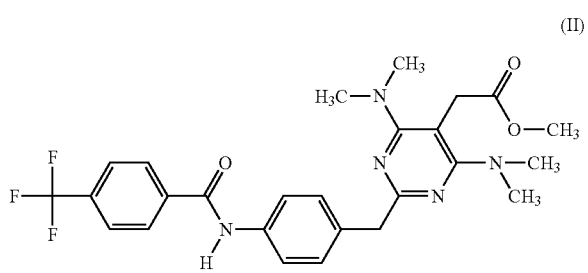 [SMILES: COC(=O)Cc1c(N(C)C)nc(Cc2ccc(NC(=O)c3ccc(C(F)(F)F)cc3)cc2)nc1N(C)C]

in the presence of a first base and of a solvent or of a mixture of solvents (also referred to as step A).

The process according to the present invention is especially suitable for large scale production of the compound of formula (I). Said process provides the compound of formula (I) in high yield and high purity. Said process further is efficient in terms of effort, energy and expenses.

Step A:

The term "hydrolysis" as used herein refers to the cleavage of the ester function by formal addition of a molecule of water. Accordingly the solvent or the mixture of solvents contains water at least in an amount sufficient to perform complete hydrolysis of the compound of formula (II), i.e. at least 1 mole of water per 1 mole of the compound of formula (II), preferably at least 5 moles of water per 1 mole of the compound of formula (II), more preferably at least 10 moles of water per 1 mole of the compound of formula (II), in particular 30 to 50 moles of water per 1 mole of the compound of formula (II).

Furthermore the solvent or the mixture of solvents used in step A preferably is a mixture of water with at least one water miscible solvent selected from ethers and/or alcohols, preferably from tetrahydrofuran and/or methanol. In particular the solvent or the mixture of solvents used in step A is a mixture consisting of 40 to 55% by volume of tetrahydrofuran, 10 to 40% by volume methanol and 15 to 50% by volume water.

In general the solvent or the mixture of solvents used in step A is used in an amount of 1.0 to 3.0 liters per 1 mole of the compound of formula (II), preferably in an amount of 1.0 to 2.0 liters per 1 mole of the compound of formula (II).

The base used according to step A (also referred to as the first base) may be selected from hydroxides or carbonates of alkali metals or alkaline earth metals, such as NaOH, LiOH, $Na_2CO_3$, $K_2CO_3$, $Cs_2CO_3$ or $Li_2CO_3$. Preferably the base used according to step A is LiOH, in particular the monohydrate of LiOH.

In general the base used according to step A is used in an amount of at least 1 mole per 1 mole of the compound of formula (II), preferably in an amount of 1.0 to 2.0 moles per 1 mole of the compound of formula (II) in particular in an amount of 1.3 to 1.7 moles per 1 mole of the compound of formula (II).

Step A of the process according to the present invention is usually performed at atmospheric pressure.

Step A of the process according to the present invention is usually performed at a temperature between 15° C. and the boiling point of the solvent or the mixture of solvents at atmospheric pressure. In particular step A is performed at a temperature of about 60° C. when a mixture consisting of 40 to 55% by volume of tetrahydrofuran, 40 to 55% by volume methanol and 5 to 20% by volume water is used as the mixture of solvents.

The reaction time for step A of the process according to the present invention depends on the reaction conditions used. In general the reaction conditions are selected in a way that the reaction time is between 1 and 10 hours, preferably between 2 and 4 hours.

Suitable equipment for performing step A of the process according to the present invention, such as double jacketed vessels, are known in the art.

In a preferred embodiment of the present invention the reaction mixture obtained in Step A of the process according to the present invention comprising a salt of the compound of formula (I) is subsequently neutralized with an acid, preferably an organic acid such as acetic acid.

In general acetic acid is used in an amount of 0.5 to 5 moles per 1 mole of the compound of formula (II), preferably in an amount of 1 to 3 moles per 1 mole of the compound of formula (II).

The compound of formula (I) may be isolated as a solid by usual means such as filtration and washing of the crude product with a solvent in which the compound of formula (I) is poorly soluble, such as methanol.

Step B:

A particular embodiment of the present invention relates to the process as previously described, wherein the compound of formula (II) is obtained by reacting a compound of formula (III)

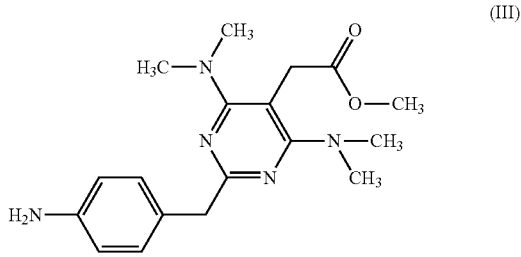 [SMILES: COC(=O)Cc1c(N(C)C)nc(Cc2ccc(N)cc2)nc1N(C)C]

(III)

with 4-trifluoromethylbenzoyl chloride in the presence of a second base and of a solvent or of a mixture of solvents (referred to as step B).

In step B 4-trifluoromethylbenzoyl chloride in general is used in an at least equimolar ratio with respect to the molar amount of the compound of formula (III). Preferably 4-trifluoromethylbenzoyl chloride is used in an amount of 1 to 1.5 moles per 1 mole of the compound of formula (III), in particular in an amount of 1.01 to 1.15 moles per 1 mole of the compound of formula (III).

The base used according to step B (also referred to as the second base) may be selected from inorganic bases, such as $Na_2CO_3$ or $K_2CO_3$, or from organic bases, such as tertiary amines or nitrogen containing heteroaromatic compounds, such as diisopropylethylamine, triethylamine or pyridine. Preferably the base used according to step B is diisopropylethylamine.

In general the base used according to step B is used in an amount of at least 1 mole per 1 mole of the compound of formula (III), preferably in an amount of 1.0 to 1.5 moles per 1 mole of the compound of formula (III), more preferably in an amount of 1.05 to 1.2 moles per 1 mole of the compound of formula (III).

The solvent or the mixture of solvents used in step B may be selected from polar aprotic solvents, such as dimethylformamide or N-methyl-2-pyrrolidon, or from alcohols, such as methanol, ethanol or isopropanol.

Surprisingly it has been found that the reaction of step B is very fast and thus highly selective. Accordingly the preferred solvent or the mixture of solvents used in step B in particular is methanol.

In general the solvent or the mixture of solvents used in step B is used in an amount of 1 to 5 liters per 1 mole of the compound of formula (II), preferably in an amount of 2.0 to 3.0 liters per 1 mole of the compound of formula (II).

Step B of the process according to the present invention is usually performed at atmospheric pressure.

Step B of the process according to the present invention is usually performed at a temperature between 15° C. and the boiling point of the solvent or the mixture of solvents at atmospheric pressure. In particular step A is performed at a temperature of about 40 to 60° C. when methanol is used as the solvent.

The reaction time for step B of the process according to the present invention depends on the addition rate of 4-trifluoromethylbenzoyl chloride. In general the reaction conditions are selected in a way that the addition time is between 0.1 and 5 hours, preferably between 0.5 and 1.5 hours.

Suitable equipment for performing step B of the process according to the present invention, such as double jacketed vessels, are known in the art.

The compound of formula (II) may be isolated as a solid by usual means such as filtration. To improve the filtration properties, ageing of the crystals can be carried out by heating to reflux after addition of 4-trifluoromethylbenzoyl chloride and before cooling down. For purification the crude product can be then washed with a solvent in which the compound of formula (II) is poorly soluble, such as isopropanol.

Step C:

Another particular embodiment of the present invention relates to the process as previously described, wherein the compound of formula (III) is obtained by hydrogenation of a compound of formula (IV) (referred to as step C)

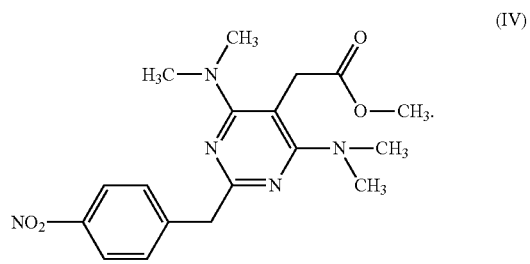 [SMILES: COC(=O)Cc1c(N(C)C)nc(Cc2ccc([N+](=O)[O-])cc2)nc1N(C)C]

(IV)

The hydrogenation of the compound of formula (IV) in step C is generally performed in the presence of a hydrogenation catalyst. Suitable hydrogenation catalysts are known in the art. In particular step C of the process according to the present invention is performed in the presence of palladium on activated charcoal.

The solvent or the mixture of solvents used in step C may be selected from inert solvents such as alcohols, esters, saturated hydrocarbons, halogenated saturated hydrocarbons, ethers or cyclic ethers and mixtures thereof. In particular the preferred solvent used in step C is a mixture of methanol and isopropyl acetate.

In general the solvent or the mixture of solvents used in step C is used in an amount of 0.01 to 5 liters per 1 mole of the compound of formula (IV), preferably in an amount of 1 to 3 liters per 1 mole of the compound of formula (IV).

The reaction according to step C of the present invention is usually performed at a hydrogen pressure of 1 to 5 bar, preferably at a hydrogen pressure of 2.0 to 3.0 bar.

Step C of the process according to the present invention is usually initiated at a temperature between 15° C. and 60° C., preferably at a temperature of 25° C. to 40° C. During hydrogenation the temperature may increase to 70° C.

The reaction time for step C of the process according to the present invention depends on the reaction conditions used. In general the reaction conditions are selected in a way that the reaction time is between 0.05 and 5 hours, preferably between 0.5 and 3 hours.

Suitable equipment for performing step C of the process according to the present invention, such as double jacket vessels or autoclaves, are known in the art.

The compound of formula (III) may be purified by replacing changing the solvent used in step C with a new solvent in which the compound of formula (III) is poorly soluble, such as isopropanol. Isopropanol may be added in an amount of 1 to 10 liters per mole of the compound of formula (III), preferably in an amount of 1 to 4 liters per mole of the compound of formula (III).

The compound of formula (III) may be isolated as a solid by usual means such as filtration and washing of the crude product with a solvent in which the compound of formula (III) is poorly soluble, such as isopropanol.

The compound of formula (III) is thus obtained as its free base.

Step D:

Another particular embodiment of the present invention relates to the process as previously described, wherein the compound of formula (IV) is obtained by reacting a compound of formula (V)

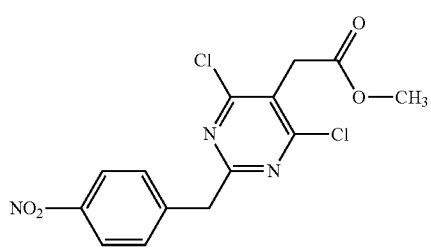

(V)

with an excess of dimethylamine in the presence of a solvent or of a mixture of solvents (referred to as step D).

In step D dimethylamine in general is used in an amount of at least 4 moles for 1 mole of the compound of formula (V). Preferably dimethylamine is used in an amount of 5 to 20 moles per 1 mole of the compound of formula (V), in particular in an amount of 7 to 15 moles per 1 mole of the compound of formula (V). Dimethylamine is preferably added neat to the reaction mixture.

The solvent or the mixture of solvents used in step D may be selected from polar solvents such as ethers, esters, amides and mixtures thereof. In particular the preferred solvent used in step D is isopropyl acetate.

In general the solvent or the mixture of solvents used in step D is used in an amount of 0.3 to 5 liters per 1 mole of the compound of formula (V), preferably in an amount of 0.7 to 2 liters per 1 mole of the compound of formula (V).

The reaction according to step D of the present invention is usually performed at a pressure of 1 to 5 bar, preferably at a pressure of 2.0 to 3.5 bar.

Step D of the process according to the present invention is usually performed at a temperature between 40° C. and 100° C., preferably at a temperature of 60° C. to 80° C.

The reaction time for step D of the process according to the present invention depends on the reaction conditions used. In general the reaction conditions are selected in a way that the reaction time is between 1 and 12 hours, preferably between 4 and 10 hours.

Suitable equipment for performing step D of the process according to the present invention, such as double jacket vessels, are known in the art.

The compound of formula (IV) may be isolated using standard techniques. However, preferably the hydrogenation of the compound of formula (IV) obtained in step D is performed without prior isolation of said compound, i.e. the crude reaction mixture obtained in step D is used as starting material for step C. In this particular embodiment the reaction mixture obtained in step D is preferably washed with water prior to performing the hydrogenation. After washing of the reaction mixture obtained in step D the reaction mixture may be diluted with a protic polar solvent such as methanol.

Step E:

Another particular embodiment of the present invention relates to the process as previously described, wherein the compound of formula (V) is obtained by reacting a compound of formula (VI)

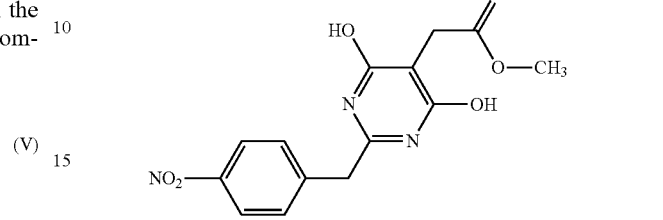

(VI)

with a chlorinating agent in the presence of a third base (referred to as step E).

The chlorinating agent used in step E may be selected from $SOCl_2$, $PCl_3$, $PCl_5$ or $POCl_3$. Preferably the chlorinating agent is $POCl_3$.

In step E the chlorinating agent in general is used in an amount of at least 1.5 moles for 1 mole of the compound of formula (VI). Preferably the chlorinating agent is used in an amount of 1.5 to 3.5 moles per 1 mole of the compound of formula (VI), in particular in an amount of 2.3 to 2.8 moles per 1 mole of the compound of formula (VI).

The base used according to step E (also referred to as the third base) may be selected from tertiary amines or nitrogen containing heteroaromatic compounds, such as triethylamine, diisopropylethylamine or pyridine. Preferably the base used according to step D is triethylamine.

In general the base used according to step E is used in an amount of at least 1 mole per 1 mole of the compound of formula (VI), preferably in an amount of 1 to 3 moles per 1 mole of the compound of formula (VI), more preferably in an amount of 1.2 to 1.8 moles per 1 mole of the compound of formula (VI).

The solvent or the mixture of solvents used in step E preferably is selected from solvents, such as aromatic hydrocarbons, halogenated hydrocarbons, esters, ethers and mixtures thereof. In particular the preferred solvent or the mixture of solvents used in step E is toluene.

In general the solvent or the mixture of solvents used in step E is used in an amount of 1 to 3 liters per 1 mole of the compound of formula (VI), preferably in an amount of 1.1 to 1.5 liters per 1 mole of the compound of formula (VI).

Step E of the process according to the present invention is usually performed at atmospheric pressure.

Step E of the process according to the present invention is usually performed at a temperature between 15° C. and the boiling point of the solvent or the mixture of solvents at atmospheric pressure. In particular step E is performed at a temperature of 90° C. to 110° C. when toluene is used as the solvent.

The reaction time for step E of the process according to the present invention depends on the reaction conditions used. In general the reaction conditions are selected in a way that the reaction time is between 1 and 10 hours, preferably between 2 and 4 hours.

Suitable equipment for performing step E of the process according to the present invention, such as double jacketed vessels, are known in the art.

In a preferred embodiment of the present invention the reaction mixture obtained in Step E of the process according to the present invention is neutralized with an inorganic base, preferably an aqueous solution of sodium hydroxide, after in vacuo removal of the excess chlorinating agent.

In general sodium hydroxide is used in an amount of 1.5 to 5 moles per 1 mole of the compound of formula (VI), preferably in an amount of 2.5 to 3.5 moles per 1 mole of the compound of formula (VI).

The compound of formula (V) may be isolated as a solid by usual means such as filtration and washing of the crude product with a solvent in which the compound of formula (V) is poorly soluble, such as methanol and/or water.

Step F:

Another particular embodiment of the present invention relates to the process as previously described, wherein the compound of formula (VI) is obtained by reacting a compound of formula (VII) or a hydrohalogenide thereof.

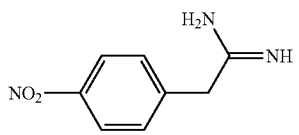

(VII)

with trimethyl 1,1,2-ethanetricarboxylate in the presence of a fourth base (referred to as step F). The compound of formula (VII) is preferably used as the hydrochloride thereof.

In step F of the process according to the present invention the trimethyl 1,1,2-ethanetricarboxylate in general is used in an amount of at least 1 mole for 1 mole of the compound of formula (VII). Preferably trimethyl 1,1,2-ethanetricarboxylate is used in an amount of 1 to 5 moles per 1 mole of the compound of formula (VII), in particular in a amount of 1.1 to 1.5 moles per 1 mole of the compound of formula (VII).

The base used according to step F (also referred to as the fourth base) may be selected from lower alkanolates of alkali metals or alkaline earth metals, such as $NaOCH_3$, $KOCH_3$ or $LiOCH_3$. Preferably the base used according to step A is sodium methylate ($NaOCH_3$).

In general the base used according to step F is used in an amount of at least 1 mole per 1 mole of the compound of formula (VII), preferably in an amount of 1.5 to 5 moles per 1 mole of the compound of formula (VII), more preferably in an amount of 2 to 3 moles per 1 mole of the compound of formula (VII).

The solvent or the mixture of solvents used in step F preferably is selected from polar protic solvents, such as alcohols, or polar aprotic solvents such as ethers, esters or amides, such as N-methyl-2-pyrrolidon or dimethylformamide, and mixtures thereof. In particular the solvent or the mixture of solvents used in step F is methanol.

In general the solvent or the mixture of solvents used in step F is used in an amount of 1 to 10 liters per 1 mole of the compound of formula (VII), preferably in an amount of 2 to 5 liters per 1 mole of the compound of formula (VII).

Step F of the process according to the present invention is usually performed at atmospheric pressure.

Step F of the process according to the present invention is usually performed at a temperature between 15° C. and the boiling point of the solvent or the mixture of solvents at atmospheric pressure. In particular step F is performed at a temperature of 35° C. to 55° C. when methanol is used as the solvent.

The reaction time for step F of the process according to the present invention depends on the reaction conditions used. In general the reaction conditions are selected in a way that the reaction time is between 1 and 10 hours, preferably between 3 and 6 hours.

Suitable equipment for performing step F of the process according to the present invention, such as double jacketed vessels, are known in the art.

In a preferred embodiment of the present invention the reaction mixture obtained in Step F of the process according to the present invention is adjusted to a pH value of 6 to 7 with acetic acid to prior to diluting the reaction mixture with water.

The compound of formula (VI) may be isolated as a solid by usual means such as filtration and washing of the crude product with a solvent in which the compound of formula (VI) is poorly soluble, such as methanol and/or water.

Step G:

Another particular embodiment of the present invention relates to the process as previously described, wherein the compound of formula (VII) or the hydrohalogenide thereof is obtained by reacting 4-nitrophenylacetonitrile with acetyl chloride in the presence of methanol and subsequently reacting the obtained intermediate with ammonia (referred to as step G).

In step G of the process according to the present invention acetyl chloride in general is used in an amount of at least 2 moles for 1 mole of 4-nitrophenylacetonitrile. Preferably acetyl chloride is used in an amount of 2.5 to 3.5 moles for 1 mole of 4-nitrophenylacetonitrile.

In step G of the process according to the present invention methanol in general is used in an amount of at least 2 moles for 1 mole of 4-nitrophenylacetonitrile. Preferably methanol is used in an amount of 4 to 6 moles for 1 mole of 4-nitrophenylacetonitrile.

The solvent or the mixture of solvents used preferably is selected from aprotic solvents, such as aromatic hydrocarbons. In particular the solvent or the mixture of solvents used is toluene.

In step G of the process according to the present invention the reaction mixture is generally concentrated in vacuo to some extent before addition of ammonia.

Ammonia in general is used in an amount of at least 1 mole for 1 mole of 4-nitrophenylacetonitrile. Preferably ammonia is used in an amount of 1 to 10 moles per 1 mole of 4-nitrophenylacetonitrile, in particular in an amount of 2 to 5 moles per 1 mole of 4-nitrophenylacetonitrile.

In step G of the process according to the present invention ammonia is preferably used as a solution of ammonia in an organic solvent, such as methanol.

The solvent or the mixture of solvents used in step G preferably is selected from protic solvents, such as alcohols, which may be mixed with aromatic hydrocarbons or other aprotic solvents. In particular the solvent or the mixture of solvents used in step G is a mixture of methanol and toluene.

In general the solvent or the mixture of solvents used for the amination in step G is used in an amount of 0.5 to 5 liters per 1 mole of 4-nitrophenylacetonitrile, preferably in an amount of 0.7 to 3 liters per 1 mole of 4-nitrophenylacetonitrile.

Step G of the process according to the present invention is usually performed at atmospheric pressure.

Step G of the process according to the present invention is usually performed at a temperature between 15° C. and 50° C. In particular step G is performed at a temperature of 18° C. to 30° C.

The reaction time for step G of the process according to the present invention depends on the reaction conditions used. In general the reaction conditions are selected in a way that the reaction time is between 1 and 10 hours, preferably between 5 and 8 hours.

Suitable equipment for performing step G of the process according to the present invention, such as double jacketed vessels, are known in the art.

In a preferred embodiment of the present invention excess ammonia and at least a part of the reaction solvent is removed in vacuo and the residue is diluted with acetone and cooled to ambient temperature, to facilitate precipitation of the compound of formula (VII).

The compound of formula (VII) may be isolated as a solid by usual means such as filtration and washing of the crude product with a solvent in which the compound of formula (VII) is poorly soluble, such as acetone.

The following examples are intended to further illustrate the present invention without limiting its scope.

Example 1

Process for preparing [4,6-bis-dimethylamino-2-[4-(4-trifluoromethylbenzoyl-amino)benzyl]pyrimidin-5-yl]acetic acid (Compound of formula (I))

Step G:

To a stirred suspension of 4-nitrophenylacetonitril (150.0 g) in toluene (900 mL) in a 2500 mL double jacketed vessel at 20±5° C. is added methanol (182 mL). To this suspension acetyl chloride (217.9 g) is slowly added over a period of 1 hour in order not to exceed a reaction temperature of 25° C. Subsequently the suspension is stirred at 25±5° C. for about 4 hours. The reaction mixture is heated to 45° C. and concentrated in vacuo to obtain a volume of approx. 950 mL of the residue. The residue is diluted with toluene (450 mL) and again concentrated in vacuo to obtain a volume of approx. 1000 mL. After cooling to 20±5° C. a solution of Ammonia in methanol (7 M, 308.7 g) is added over a period of 10 minutes. The obtained suspension is stirred for additional 2 hours, heated to 45° C. and concentrated in vacuo to obtain a volume of the residue of approx. 600 mL. The residue is cooled to 20±5° C. and treated with acetone (450 mL). The reaction mixture is stirred for 30 minutes. The solid is filtered off, washed and dried in vacuo at 35° C. to yield 2-(4-nitrophenyl)acetamidine hydrochloride as colorless crystals in an amount of 185.8 g (yield: 95%; HPLC-purity: 99.95%).

Step F:

To a stirred suspension of 2-(4-nitrophenyl)acetamidine hydrochloride (100 g, obtained according to step G) in methanol (850 mL) in a 2500 mL double jacketed vessel melted trimethyl-1,1,2-ethantricarboxylat having a temperature of about 65° C. is added. The reaction mixture is heated to 40±5° C. A solution of sodium methanolate (30% in methanol, 230 g) is added over a period of 10 minutes. The reaction mixture is stirred at 40±5° C. for an additional 4 hours. The reaction mixture is adjusted to a pH value of 6.2 with acetic acid (76.6 g), 500 mL of water are added and the reaction mixture is stirred at 40±5° C. for about 2 hours. After cooling to 20±5° C. the solid is filtered off, washed with methanol (225 mL) and with a mixture of methanol and water (175 mL). The solid is dries in vacuo at 60° C. to yield 238.6 g of a crude product containing [4,6-dihydroxy-2-(4-nitrobenzyl)-pyrimidin-5-yl]-acetic acid methyl ester in an amount of 119.3 g (yield: 81%; HPLC-purity: 97.5%).

Step E:

To a stirred suspension of [4,6-dihydroxy-2-(4-nitrobenzyl)-pyrimidin-5-yl]acetic acid methyl ester (200 g, obtained according to step F) in toluene (800 mL) in a 2500 mL double jacketed vessel at 20±5° C. is added 245 g POCl$_3$. To this reaction mixture triethylamine (95 g) is added over a period of 5 minutes. The reaction mixture is heated to 103±2° C. (reflux conditions) and stirred for 3 hours. The excess POCl$_3$ is removed in vacuo. The resulting suspension is cooled to 25±5° C. and 800 mL of methanol is added. Subsequently an aqueous solution of NaOH (13% by weight, 164 g) is added and the reaction mixture is stirred at 20±5° C. for 30 minutes. The solid is filtered off and washed subsequently with methanol (600 mL), deionized water (440 mL) and again with methanol (200 mL). The crystalline product is dried in vacuo at 30° C. to yield [4,6-dichloro-2-(4-nitrobenzyl)pyrimidin-5-yl]acetic acid methyl ester in an amount of 201 g (yield: 90%; HPLC-purity: 98.2%).

Step D and C:

a) In an inertised autoclave [4,6-dichloro-2-(4-nitrobenzyl)pyrimidin-5-yl]acetic acid methyl ester (200 g, obtained according to step E) is suspended in 600 mL of acetic acid isopropyl ester. The autoclave is evacuated and to the stirred suspension neat dimethylamin (232.5 g) is added at a pressure of up to 2.5 bar and at a temperature cooled to 20±5° C. over a period of about 90 minutes. The reaction mixture is heated to 70±5° C. and stirred for another 4 hours. Deionized water (400 mL) is added to the reaction mixture. The reaction mixture is heated to 62±3° C. After separation of phases the aqueous phase is removed to yield an organic solution comprising [4,6-bis-dimethylamino-2-(4-nitrobenzyl)pyrimidin-5-yl]acetic acid methyl ester.

b) The organic solution obtained in a) (800 mL, corresponding to 208 g of 4,6-bis-dimethylamino-2-(4-nitrobenzyl)pyrimidin-5-yl]acetic acid methyl ester) was transferred to a hydrogenation vessel and diluted with 400 mL of methanol. Palladium on activated charcoal (10% by weight of Pd, 1000 mg) was added and the hydrogenation was performed at 30-60° C. and approximately 3 bar of hydrogen pressure for 1 hour. The catalyst was removed by filtration and washed with 300 mL of methanol. The obtained filtrate was transferred to a double jacketed vessel, heated to 60±5° C. and concentrated in vacuo to obtain 480 mL of a residue. To the residue was added 1000 mL of isopropanol. After heating to 60±5° C. the resulting suspension is cooled to 0±5° C. and stirred for one hour. The solid is filtered off, washed with 400 mL of isopropanol and dried in vacuo at 50° C. to yield [4,6-bis-dimethylamino-2-(4-aminobenzyl)pyrimidin-5-yl]acetic acid methyl ester in an amount of 164.0 g (yield: 85% (overall yield for steps D and E); HPLC-purity: 98.2%).

Step B:

To a stirred suspension of [4,6-bis-dimethylamino-2-(4-aminobenzyl)pyrimidin-5-yl]acetic acid methyl ester (100 g, obtained according to step C) in 700 mL of methanol in a 1500 mL double jacketed vessel at 20±5° C. is added diisopropylethylamin (41.4 g) over a period of 30 minutes while heating the reaction mixture to 50±5° C. 4-Trifluoromethylbenzoic acid chloride (63.8 g) is added during further 30 minutes. The reaction mixture is stirred for 15 minutes at 50±5° C. and subsequently heated to 65±5° C. (reflux conditions) and stirred for another 30 minutes. The resulting suspension is gradually cooled to 5±5° C. over a period of 2 hours and stirred at this temperature for 1 hour. The solid is filtered off, washed with 200 mL of isopropanol and dried in vacuo at 50° C. to yield [4,6-bis-dimethylamino-2-[4-(4-trifluoromethylbenzoylamino)benzyl]pyrimidin-5-yl]acetic acid methyl ester in an amount of 135.8 g (yield: 90%; HPLC-purity: 99.5%).

Step A:

A stirred suspension of [4,6-bis-dimethylamino-2-[4-(4-trifluoromethylbenzoylamino)-benzyl]pyrimidin-5-yl]acetic acid methyl ester (50 g, obtained according to step B) and lithium hydroxide monohydrate (6.3 g) in a mixture of 100 mL of tetrahydrofurane and 50 mL of methanol in a 1500 mL double jacketed vessel is heated to 60±5° C. over a period of 1 hour. Deionized water (75 mL) is slowly added. The obtained solution is stirred for 2 hours at 60±5° C. A solution of acetic acid (11.6 g) in 50 mL of methanol is added at 60±5° C. The resulting suspension is gradually cooled to 5±5° C. over a period of 2 hours and stirred at this temperature for another 30 minutes. The solid is filtered off, washed with 200 mL of methanol and dried in vacuo at 50° C. to yield [4,6-bis-dimethylamino-2-[4-(4-trifluoromethyl-benzoyl-amino)benzyl]pyrimidin-5-yl]acetic acid (compound of formula (I)) in an amount of 43.65 g (yield: 90%; HPLC-purity: 99.6%).

The invention claimed is:

1. A process for preparing a compound of formula (I)

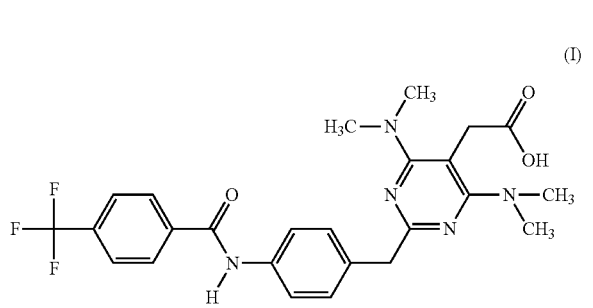 [SMILES: CN(C)c1nc(Cc2ccc(NC(=O)c3ccc(C(F)(F)F)cc3)cc2)nc(N(C)C)c1CC(=O)O]

the process comprising reacting a compound of formula (III)

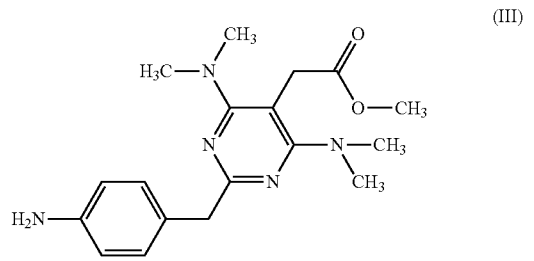 [SMILES: COC(=O)Cc1c(N(C)C)nc(Cc2ccc(N)cc2)nc1N(C)C]

with 4-trifluoromethylbenzoyl chloride in the presence of a second base and methanol to obtain a compound of formula (II)

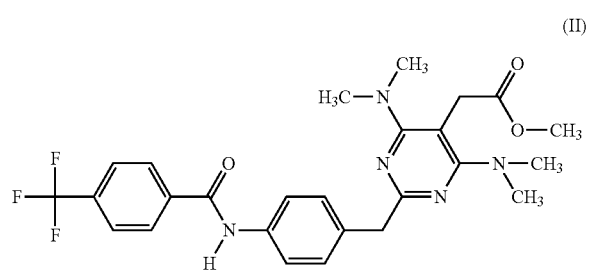 [SMILES: COC(=O)Cc1c(N(C)C)nc(Cc2ccc(NC(=O)c3ccc(C(F)(F)F)cc3)cc2)nc1N(C)C]

and then hydrolyzing the compounds of formula (II) in the presence of a first base and of a solvent or of a mixture of solvents to obtain the compound of formula (I).

2. The process according to claim 1, wherein the first base is the monohydrate of LiOH.

3. The process according to claim 1, wherein the solvent or the mixture of solvents is a mixture of tetrahydrofuran, methanol, and water.

4. The process according to claim 1, wherein the obtained reaction mixture comprising a salt of the compound of formula (I) is subsequently neutralized with acetic acid.

5. The process according to claim 1, wherein the second base is diisopropylethylamine.

6. The process according to claim 1, wherein the compound of formula (III) is obtained by hydrogenation of a compound of formula (IV)

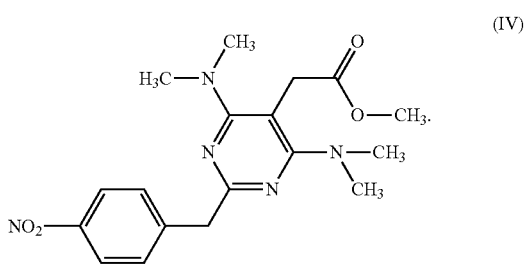

7. The process according to claim 6, wherein the hydrogenation takes place in the presence of palladium on activated charcoal.

8. The process according to claim 6, wherein the compound of formula (III) is isolated from isopropanol as its free base.

9. The process according to claim 6, wherein the compound of formula (IV) is obtained by reacting a compound of formula (V)

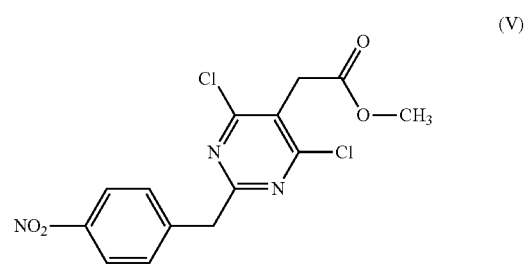 [SMILES: COC(=O)Cc1c(Cl)nc(Cc2ccc([N+](=O)[O-])cc2)nc1Cl]

with an excess of dimethylamine in the presence of a solvent or of a mixture of solvents.

10. The process according to claim 9, wherein the solvent or the mixture of solvents is isopropyl acetate.

11. The process according to claim 9, wherein the hydrogenation of the compound of formula (IV) is subsequently performed without prior isolation.

12. The process according to claim 11, wherein the reaction mixture is washed with water prior to performing the hydrogenation.

13. The process according to claim 9, wherein the compound of formula (V) is obtained by reacting a compound of formula (VI)

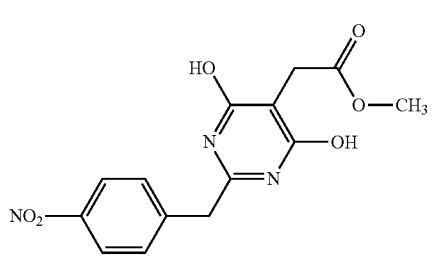

(VI)

with a chlorinating agent in the presence of a third base.

14. The process according to claim 13, wherein the chlorinating agent is POCl₃.

15. The process according to claim 13, wherein the third base is triethylamine.

16. The process according to claim 9, wherein the compound of formula (VI) is obtained by reacting a compound of formula (VII) or a hydrohalogenide thereof (VII)

with trimethyl 1,1,2-ethantricarboxylate in the presence of a fourth base.

17. The process according to claim 16 wherein the fourth base is sodium methylate.

18. The process according to claim 16, wherein the compound of formula (VII) or the hydrohalogenide thereof is obtained by reacting 4-nitrophenylacetonitril in the presence of methanol and acetyl chloride and subsequently reacting the obtained intermediate with ammonia.

* * * * *